(12) United States Patent
Lin et al.

(10) Patent No.: US 11,850,321 B2
(45) Date of Patent: Dec. 26, 2023

(54) CASING AND MANUFACTURING METHOD THEREOF

(71) Applicant: Acer Incorporated, New Taipei (TW)

(72) Inventors: Wen-Hsin Lin, New Taipei (TW); Wen-Chieh Tai, New Taipei (TW); Cheng-Nan Ling, New Taipei (TW)

(73) Assignee: Acer Incorporated, New Taipei (TW)

( * ) Notice: Subject to any disclaimer, the term of this patent is extended or adjusted under 35 U.S.C. 154(b) by 286 days.

(21) Appl. No.: 17/182,233

(22) Filed: Feb. 23, 2021

(65) Prior Publication Data

US 2022/0096691 A1 Mar. 31, 2022

(30) Foreign Application Priority Data

Sep. 25, 2020 (TW) ................. 109133337

(51) Int. Cl.
| | | |
|---|---|---|
| *A45C 11/00* | (2006.01) | |
| *A61L 2/232* | (2006.01) | |
| *A61L 101/02* | (2006.01) | |

(52) U.S. Cl.
CPC .............. *A61L 2/232* (2013.01); *A45C 11/00* (2013.01); *A45C 2011/001* (2013.01); *A45C 2011/002* (2013.01); *A45C 2011/003* (2013.01); *A61L 2101/02* (2020.08)

(58) Field of Classification Search
CPC .......... C09D 175/04; C09D 1/00; C09D 5/14; C09D 11/102; C09D 11/38; C09D 11/107; C09D 11/033; C09D 11/54; C09D 11/03; C09D 11/322; C09D 11/40; C09D 11/037; C09D 11/10; C09D 11/106; C09D 11/326; C09D 11/50; G02B 5/00; G02B 5/005; G02B 5/08; A45C 11/00; A45C 13/42; A45C 2011/001; A45C 2011/002; A45C 2011/003

See application file for complete search history.

(56) References Cited

U.S. PATENT DOCUMENTS

| | | |
|---|---|---|
| 2003/0081203 A1 | 5/2003 | Chen et al. |
| 2004/0161690 A1 | 8/2004 | Sakurai et al. |
| 2005/0287112 A1 | 12/2005 | Kwon et al. |
| 2014/0336557 A1 | 11/2014 | Durdag et al. |

FOREIGN PATENT DOCUMENTS

| | | | | |
|---|---|---|---|---|
| JP | 2011242759 | * | 12/2011 | ........... G02B 5/3041 |
| KR | 101860896 | * | 7/2018 | ............. C04B 33/20 |
| TW | 589929 | | 6/2004 | |
| TW | I447424 | | 8/2014 | |

OTHER PUBLICATIONS

JP2011242759 translation (Year: 2011).*
KR101860896 translation (Year: 2018).*

* cited by examiner

*Primary Examiner* — Audrea B Coniglio
(74) *Attorney, Agent, or Firm* — JCIPRNET

(57) ABSTRACT

The disclosure provides a casing including a substrate, a transparent fluorescent identifying part, and a transparent antibacterial film. The transparent fluorescent identifying part is disposed on the substrate. The transparent antibacterial film covers the substrate and the transparent fluorescent identifying part. A method of manufacturing the casing is also provided.

5 Claims, 3 Drawing Sheets

CASING AND MANUFACTURING METHOD THEREOF

CROSS-REFERENCE TO RELATED APPLICATION

This application claims the priority benefit of Taiwan application serial no. 109133337, filed on Sep. 25, 2020. The entirety of the above-mentioned patent application is hereby incorporated by reference herein and made a part of this specification.

BACKGROUND

Technical Field

The disclosure relates to a casing, particularly to a casing and a manufacturing method thereof.

Description of Related Art

The casing is adapted as an exterior element of an electronic product, and the exterior element of the casing often comes in touch with its user's limbs, making the exterior surface of the casing easy to breed bacteria. With the rising awareness of health and hygiene, antibacterial treatment on the exterior surface of the casing has become a trend. As the user's limbs touch the exterior surface of the case frequently, the antibacterial protection on the exterior surface of the casing may be damaged or become invalid. Currently, there is no quick and intuitive determination mechanism for the user to determine the antibacterial protection on the exterior surface of the casing.

SUMMARY

The present disclosure provides a casing and a manufacturing method thereof, capable of assisting a user to determine the antibacterial protection of the casing in a quick and intuitive way.

The present disclosure provides a casing, including a substrate, a transparent fluorescent identification part, and a transparent antibacterial film. The transparent fluorescent identification part is disposed on the substrate. The transparent antibacterial film covers the substrate and the transparent fluorescent identification part.

The present disclosure also provides a manufacturing method for a casing, including the following steps. First, the substrate is provided. Then, a transparent fluorescent ink is printed on the substrate to form a transparent fluorescent identification part. Afterwards, a transparent antibacterial coating is applied on the transparent fluorescent identification part and the substrate to form a transparent antibacterial film, in which the transparent antibacterial film covers the substrate and the transparent fluorescent identification part.

Based on the above, the casing of the present disclosure adopts a quick and intuitive determination mechanism for the user to determine the antibacterial protection on the exterior surface of the casing. Furthermore, the user only needs to irradiate the exterior surface of the casing with ultraviolet light to observe the transparent fluorescent identification part, and determine whether the antibacterial protection on the exterior surface of the casing is still effective based on whether the transparent fluorescent identification part is damaged.

In order to make the above-mentioned features and advantages of the present disclosure more comprehensible, the following embodiments are described in detail in cooperation with the accompanying drawings.

DESCRIPTION OF THE EMBODIMENTS

Figure 1:
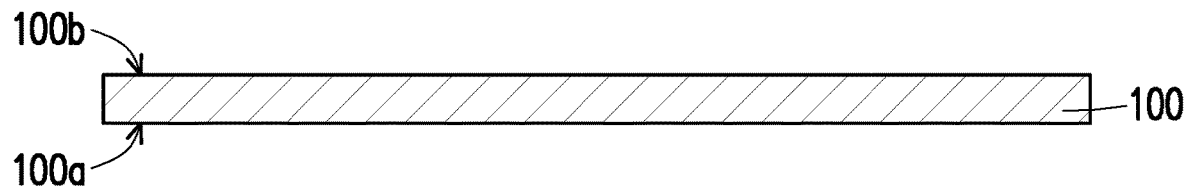
FIG. 1 to FIG. 6 are schematic cross-sectional views of a manufacturing process of a casing according to an embodiment of the present disclosure.

FIG. 1 to FIG. 6 are schematic cross-sectional views of a manufacturing process of a casing according to an embodiment of the present disclosure. In FIG. 1, first, a substrate 100 is provided, and the material of the substrate 100 may be aluminum alloy, magnesium alloy, aluminum-magnesium alloy, or magnesium-lithium alloy, but the substrate 100 is not limited to the foregoing materials. Specifically, the substrate 100 has a first surface 100a, and a second surface 100b opposite to the first surface 100a. The first surface 100a may be adapted as the inner surface of the casing 10, and the second surface 100b may be adapted as part of the exterior surface of the casing. Also, the second surface 100b may undergo several surface protection treatments to acquire the anti-oxidation, anti-corrosion, or anti-bacterial capabilities.

Figure 2:
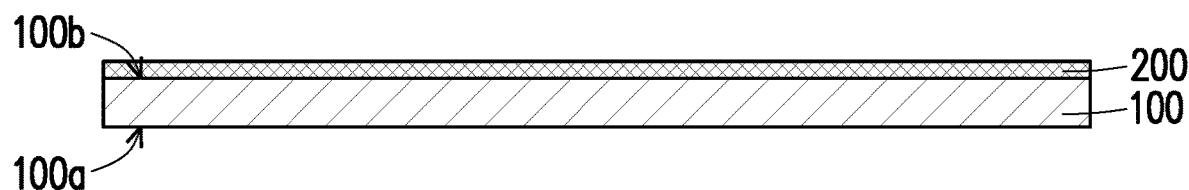
Figure 3:
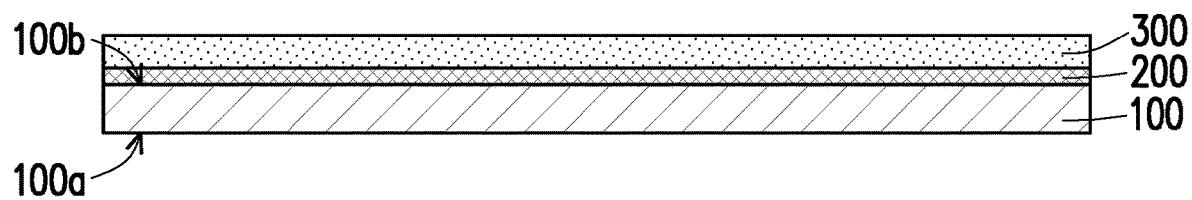

Next, a paint is sprayed on the second surface 100b of the substrate 100 to form a paint layer 200, as shown in FIG. 2. Then, the transparent film 300 is attached to the paint layer 200, as shown in FIG. 3. More specifically, the paint layer 200 covers the second surface 100b, and the transparent film 300 covers the paint layer 200. Since the transparent film 300 allows light to pass through, the casing may exhibit a metallic texture based on the cooperation of the paint layer 200 and the transparent film 300.

Figure 4:
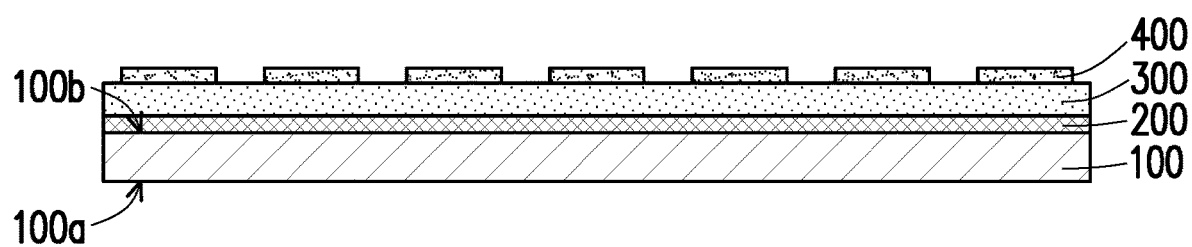

Next, in FIG. 4, a transparent fluorescent ink is printed on the transparent film 300 to form a transparent fluorescent identification part 400. Specifically speaking, the transparent film 300 is located between the transparent fluorescent identification part 400 and the paint layer 200, or to put it this way, the transparent film 300 is located between the transparent fluorescent identification part 400 and the substrate 100, whereas the transparent fluorescent identification part 400 only covers partially the transparent film 300, and may be a transparent fluorescent pattern layer composed of transparent fluorescent patterns, transparent fluorescent symbols and transparent fluorescent texts. Under normal circumstances, it is difficult for the user to observe transparent fluorescent patterns, transparent fluorescent symbols, and transparent fluorescent texts.

Figure 5:
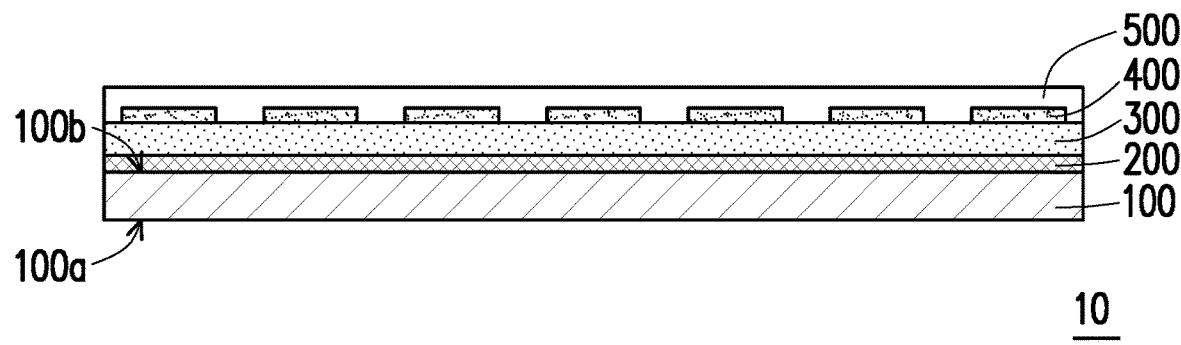

Next, in FIG. 5, a transparent antibacterial coating is sprayed on the transparent fluorescent identification part 400 and the transparent film 300 to form a transparent antibacterial film 500. In other words, the transparent antibacterial film 500 covers the transparent fluorescent identification part 400 and the transparent film 300. For example, the transparent antibacterial film 500 may be a transparent nanosilver antibacterial film, but the composition or type of the transparent antibacterial film 500 is not limited thereto.

Note that the substrate 100 is adapted as the main body of the casing, and the paint layer 200, the transparent film 300, the transparent fluorescent identification part 400, and the transparent antibacterial film 500 are sequentially formed on the substrate 100. That is to say, the substrate 100 is sequentially covered by the paint layer 200, the transparent film 300, the transparent fluorescent identification part 400, and the transparent antibacterial film 500, whereas the transparent antibacterial film 500 serves as the outermost layer of the casing, such that the outer surface of the transparent antibacterial film 500 which is exposed to the environment may be regarded as the exterior surface of the casing and has the antibacterial protection.

Figure 6:
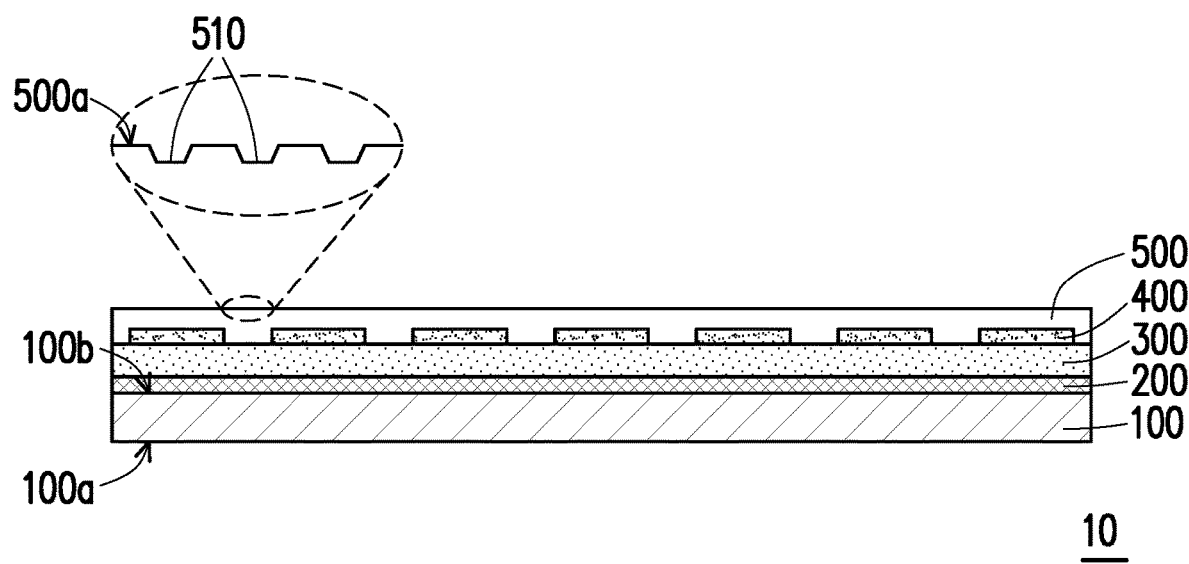

Please refer to FIG. 6, in which a texture processing process is adopted to form a texture pattern 510 on the outer surface 500a of the transparent antibacterial film 500, and it is the principle for the depth of the texture pattern 510 not to damage the transparent fluorescent identification part 400. So far, the manufacture of the casing 10 has been roughly completed. When light irradiates the outer surface 500a of the transparent antibacterial film 500 with the texture pattern 510, the reflected light is diffused due to the texture pattern 510, achieving the anti-glare effect.

Furthermore, the casing 10 may be applied to various electronic products, such as a tablet computer, a smart phone, or a notebook. The transparent antibacterial film 500 serves as the outermost layer in the casing 10, so the outer surface of the transparent antibacterial film 500 exposed to the environment may be regarded as the exterior surface of the casing 10 and has the antibacterial protection. Once the user decides to determine the antibacterial protection of the transparent antibacterial film 500, the user only needs to irradiate the casing 10 with ultraviolet light and observe the transparent fluorescent identification part 400.

After the casing 10 is irradiated with ultraviolet light, the fluorescent identification part 400 reacts with the ultraviolet light, so that the user is able to observe the integrity of the transparent fluorescent pattern, the transparent fluorescent symbols, or the transparent fluorescent texts. Assuming that the observed transparent fluorescent patterns, transparent fluorescent symbols, and transparent fluorescent texts are worn out, it indicates that the transparent antibacterial film 500 has been worn out at a certain degree, arising doubts of insufficient antibacterial power. The above determination mechanism is fast and intuitive for the users.

Note that after irradiating the casing with ultraviolet light, if the user does not observe any transparent fluorescent patterns, transparent fluorescent symbols, and transparent fluorescent texts at all, it means that the casing may not have been treated with antibacterial treatment.

In summary, the casing of the present disclosure provides a quick and intuitive determination mechanism for the user to determine the antibacterial protection on the exterior surface of the casing. And the transparent fluorescent identification part disposed on the substrate may be presented in the form of transparent fluorescent patterns, transparent fluorescent symbols, and transparent fluorescent texts. In addition, the transparent antibacterial film acts the outermost layer of the casing, so the outer surface of the transparent antibacterial film exposed to the environment may be regarded as the exterior surface of the casing and has the antibacterial protection. Once the user decides to determine the antibacterial protection on the exterior surface of the casing, the user only needs to irradiate the exterior surface of the casing with ultraviolet light to observe the transparent fluorescent identification part, and determine whether the antibacterial protection on the exterior surface of the casing is still effective based on whether the transparent fluorescent patterns, transparent fluorescent symbols, and/or transparent fluorescent texts are damaged.

Although the present disclosure has been disclosed in the above embodiments, it is not intended to limit the present disclosure. Anyone with ordinary knowledge in the art can make some modifications and changes without departing from the spirit and scope of the present disclosure. Therefore, the scope of protection of the present disclosure shall be subject to those defined by the claims.

What is claimed is:

1. A casing, comprising:
   a substrate;
   a transparent fluorescent identification part, disposed on the substrate and formed by a transparent fluorescent ink; and
   a transparent antibacterial film, covering the substrate and the transparent fluorescent identification part.

2. The casing according to claim 1, wherein the transparent antibacterial film comprises a transparent nanosilver antibacterial film, and is treated with a texture-pattern treatment.

3. The casing according to claim 1, further comprising:
   a transparent film, covering the substrate, and covered by the transparent antibacterial film, wherein the transparent fluorescent identification part is disposed on the transparent film, and the transparent film is located between the transparent fluorescent identification part and the substrate.

4. The casing according to claim 3, further comprising:
   a paint layer, covering the substrate, wherein the transparent film covers the paint layer, and the paint layer is located between the transparent film and the substrate.

5. The casing according to claim 1, wherein the transparent fluorescent identification part comprises a transparent fluorescent pattern layer.

* * * * *